(12) United States Patent
Gomez Rivas et al.

(10) Patent No.: US 9,040,922 B2
(45) Date of Patent: May 26, 2015

(54) THZ FREQUENCY RANGE ANTENNA

(75) Inventors: Jaime Gomez Rivas, Eindhoven (NL);
Vincenzo Giannini, Viggiano (IT);
Audrey Anne-Marie Berrier,
Eindhoven (NL); Stefan Alexander Maier, London (GB); Marion Matters-Kammerer, Eindhoven (NL);
Lorenzo Tripodi, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 216 days.

(21) Appl. No.: 13/375,776

(22) PCT Filed: Jun. 4, 2010

(86) PCT No.: PCT/EP2010/057846
§ 371 (c)(1),
(2), (4) Date: Dec. 2, 2011

(87) PCT Pub. No.: WO2010/139791
PCT Pub. Date: Dec. 9, 2010

(65) Prior Publication Data
US 2012/0074323 A1 Mar. 29, 2012

(30) Foreign Application Priority Data

Jun. 3, 2009 (EP) .................................... 09161766
Oct. 15, 2009 (EP) .................................... 09173166

(51) Int. Cl.
| | | |
|---|---|---|
| G01J 5/02 | (2006.01) | |
| G01J 3/42 | (2006.01) | |
| G01J 3/02 | (2006.01) | |
| G01N 21/3581 | (2014.01) | |
| G01N 21/3563 | (2014.01) | |

(52) U.S. Cl.
CPC .... *G01J 3/42* (2013.01); *G01J 3/02* (2013.01); *G01J 3/0237* (2013.01); *G01J 3/0259* (2013.01); *G01N 21/3581* (2013.01); *G01N 21/3563* (2013.01)

(58) Field of Classification Search
USPC ...................................................... 250/341.1
See application file for complete search history.

(56) References Cited

U.S. PATENT DOCUMENTS

| | | |
|---|---|---|
| 5,034,753 A | 7/1991 | Weber |
| 5,729,017 A | 3/1998 | Brener |
| 6,018,289 A | 1/2000 | Sekura |
| 6,560,165 B1 | 5/2003 | Barker |
| 6,933,581 B2 | 8/2005 | Edamura |

(Continued)

FOREIGN PATENT DOCUMENTS

WO 2004023566 A1 3/2004

OTHER PUBLICATIONS

Jan Soderkvist and Klas Hjort, J. Micromech. Microeng. 4 (1994) 28-34,"The piezoelectric effect of GaAs used for resonators and resonator sensors".*

(Continued)

*Primary Examiner* — David Porta
*Assistant Examiner* — Hugh H Maupin

(57) ABSTRACT

A THz frequency range antenna is provided which comprises: a semiconductor film (3) having a surface adapted to exhibit surface plasmons in the THz frequency range. The surface of the semiconductor film (3) is structured with an antenna structure (4) arranged to support localized surface plasmon resonances in the THz frequency range.

15 Claims, 3 Drawing Sheets

(56) References Cited

U.S. PATENT DOCUMENTS

| | | |
|---|---|---|
| 7,607,431 B1 | 10/2009 | Cruitt |
| 2002/0097156 A1 | 7/2002 | Broas |
| 2008/0137068 A1* | 6/2008 | Ouchi et al. .................... 356/51 |
| 2013/0248713 A1* | 9/2013 | Gelmont et al. ........... 250/338.4 |

OTHER PUBLICATIONS

Nagel, M. et al "THz Biosensing Devices; Fundamentals and Technology" Journal of Physics: Condensed Matter, vol. 18, May 2006, pp. S601-S618.

Gomez Rivas, J. et al "Low-Frequency Active Surface Plasmon Optics on Semiconductors" Applied Physics Letters, vol. 88, No. 8, Feb. 2006, pp. 082106-1-082106-3.

Yang, R. et al "Terahertz Wave Detection Performance of Photoconductive Antennas: Role of Antenna Structure and Gate Pulse Intensity" Journal of Applied Physics, vol. 97, No. 10, May 2005, pp. 103103-1-103103-6.

Liu, T.A. et al "Dependence of Terahertz Radiation on Gap Sizes of Biased Multi-Energy Arsenic-Ion-Implanted and Semi-Insulating GaAs Antennas" Applied Physics B Lasers and Optics, vol. 95, 2009, pp. 739-744.

Muskens, O.L. et al "Optical Scattering Resonances of Single and Coupled Dimer Plasmonic Nanoantennas" Opticas Express, vol. 15, No. 26, Dec. 2007, pp. 17736-17746.

Gu, Ping et al "Detection of Terahertz Radiation from Longitudinal Optical Phonon-Plasmon Coupling Modes in InSb film using an Ultrabroadband Photoconductive Antenna", Applied Physics Letters, vol. 77, No. 12, 2000.

* cited by examiner

THZ FREQUENCY RANGE ANTENNA

FIELD OF INVENTION

The present invention relates to a THz frequency range antenna. More specifically, it relates to a tunable THz frequency range antenna based on semiconductor material.

BACKGROUND OF THE INVENTION

In the context of the present application, the term THz frequency range designates the range of electromagnetic frequencies between 0.1 to 30 THz. This frequency range corresponds to a range of wavelengths between 10 to 3000 μm or an energy range of 0.4 to 120 meV). The THz frequency range is thus located intermediate between infrared radiation and microwave radiation. THz frequencies offer significant scientific and technological applications with regard to e.g. sensing technology, imaging technology, communication technology, and spectroscopy. For example, recent advances in THz time resolved spectroscopy have allowed the study of conductivity processes in novel organic and inorganic electronic materials with picosecond resolution.

The range of low energy excitations involved allows non-destructive inspection of a large variety of materials. Further, since electromagnetic wavelengths in the THz frequency range are capable of exciting low frequency vibrational modes of condensed phase media as well as vibrational and rotational transitions in molecules, often specific interaction takes place such that a THz frequency absorption spectrum provides a fingerprint of the molecules under examination.

Due to these features of electromagnetic THz radiation, it can for instance advantageously be used to perform spectroscopy of chemical and biological molecules and agents which comprise resonance frequencies being too low to be detected by other known means, such as infrared spectroscopy. It has already been reported that THz frequency range spectroscopy provides interesting aspects with regard to pharmaceutical applications and with regard to security applications, such as detection of explosives and the like.

However, although there are many interesting applications which could advantageously exploit the electromagnetic THz frequency range, only few methods and devices exploiting THz frequencies have been realized thus far. Partly, this results from the fact that sensing at THz frequencies poses new problems which have to be tackled before e.g. THz spectroscopy devices can be realized in a convenient and compact manner. One problem which occurs in the context of THz spectroscopy is that known tabletop THz sources provide relatively low power. This results in limited sensitivity of the known devices. Thus, in order to exploit the promising features offered by the THz frequency range for novel applications, devices will have to be developed which offer higher detection sensitivity and selectivity with regard to such frequencies.

With regard to applications in other frequency ranges of the electromagnetic frequency spectrum, in particular for the optical frequency range, antennas have been developed which exploit plasmonic resonances. For example, it has been shown that suitable plasmonic resonant structures can be created by metal structures. Studies have been performed in which antennas of this type have shown an enhanced interaction with an incoming field and in which theoretical suitability of such antennas for sensing purposes in the optical frequency range has been demonstrated. With regard to wavelengths at 10 μm, sensing has already been demonstrated using metal nanorods, the plasmonic resonance of which can couple to vibrational resonances of the material to detect. However, at THz frequencies metals have a large permittivity value (both in the real part and in the imaginary part) and thus the known concepts are not suited for providing THz frequency range antennas.

SUMMARY OF THE INVENTION

It is an object of the present invention to provide a THz frequency range antenna, an electronic system with such an antenna, and a system for distinguishing between a THz signal and background noise which are capable of providing high degrees of both sensitivity and selectivity. Further, the devices shall be tunable with regard to their operating frequencies.

This object is solved by a THz frequency range antenna according to claim 1. The THz frequency range antenna comprises a semiconductor film having a surface adapted to exhibit surface plasmons in the THz frequency range. The surface of the semiconductor film is structured to form an antenna structure arranged to support localized surface plasmon resonances in the THz frequency range. Since the THz frequency range antenna comprises the semiconductor film, the carrier concentration and/or carrier mobility in the material can be easily changed, e.g. by changes in temperature, electrical voltages applied, optical excitation, and the like. In this way, the resonance frequency of surface plasmons can be conveniently adjusted/tuned. The plasmonic resonances strongly depend on the dielectric constant of the antenna and its dielectric environment. Further, the antenna structure can be conveniently structured on or in the surface of the semiconductor film using state of the art semiconductor processing techniques such as lithography and dry and/or wet etching. Further, suitable semiconductor materials exist which at THz frequencies have permittivity values corresponding to the permittivity values of metals at optical frequencies. It has been found that THz frequency range antennas fabricated from semiconductor materials having plasma resonance in the THz frequency range can provide enhanced detection sensitivity. By suitable design of the antenna structure the electric field of the localized surface plasmon resonance can be locally enhanced which in sensor applications induces an increased interaction between the THz radiation and the object of the sensing. As a consequence, improved sensitivity is expected. Further, with such a THz frequency range antenna, field enhancements can be tailored and resonances can be shifted.

Preferably, the antenna structure comprises at least two elements structured in or on the surface of the semiconductor film and spaced from each other in a direction in parallel to the surface of the semiconductor film by a gap. It has been shown that such a structure is capable of generating a local electric field enhancement of several orders of magnitude due to plasmonic resonances in the THz regime. Further, the achieved enhancement of the electric field is dependent on the shape of the antenna structure and the gap size. Thus, the electric field enhancement can be conveniently tuned by changing these parameters. The gap should be arranged along the direction of excitation of the surface plasmons.

Preferably, the gap has a width in the range between 10 nm and 10 μm, preferably between 50 nm and 200 nm. It has been found that such a width of the gap provides suitable electric field enhancements.

If the antenna structure consists of the same material as the semiconductor film the antenna structure can be conveniently structured in the surface of the semiconductor film by known semiconductor processing techniques.

Preferably, the antenna structure has dimensions in the order of 10 μm to 1000 μm in directions parallel to the surface of the semiconductor film and dimensions in the order of 0.5 μm to 100 μm in the direction perpendicular to the surface of the semiconductor film. It has been found that antenna structures comprising these dimensions are particularly suited for achieving the desired field enhancement and localization of surface plasmon resonances.

According to one aspect, a functionalized surface adapted to attach pre-determined molecules is provided. The functionalized surface can preferably be provided in a region around the antenna structure and/or in the region of the gap. In this case, chemical compounds comprising pre-determined molecules can be sensed with particular reliability.

Preferably, the semiconductor film has thickness in the range between 0.5 μm and 300 μm. It has been found that semiconductor films having such a thickness of a few μm are particularly suited for exhibiting the exploited surface plasmon resonances.

Preferably, the semiconductor film is arranged on a substrate which is transparent for electromagnetic radiation in the THz frequency range. A particularly suited substrate is quartz. In this case, surface plasmon resonances in the THz frequency range can be reliably generated.

If the THz frequency range antenna is adapted for being inserted between a THz frequency generator and a THz frequency detector, the THz frequency surface plasmons can be reliably generated on the semiconductor surface and interaction in the region of the antenna can be detected by the THz frequency detector.

Preferably, the THz frequency range antenna comprises a piezoelectric substrate or a piezoelectric intermediate layer. For example, the semiconductor film can be formed on such a piezoelectric structure. In this case, the dimensions and or shape of the antenna structure can be changed exploiting the piezoelectric properties of the piezoelectric element. As a consequence, adjustment of the properties of the antenna is achieved in a particularly convenient manner.

Preferably, the semiconductor film comprises InSb or InAs (or any high mobility semiconductor material) as a base material. These semiconductor materials are particularly suited for the application due to their low bandgap, low electron effective mass, and high electron mobility. This allows sharp and well defined resonances. However, it should be noted that the use of other III-V semiconductor materials is also possible (with lower performances expected). The term "base material" is used to clarify that the semiconductor film does not necessarily need to comprise pure material but doping (as commonly practiced with regard to semiconductors) or other modifications are possible (and even desired).

Preferably, the antenna structure is arranged such that an electric field of the surface plasmon resonances is locally enhanced in the region of the antenna structure. In this case, an increased sensitivity is achieved. Such enhancement can e.g. be achieved by the antenna structure comprising two parts separated by a gap along the direction of excitation of surface plasmons. Enhancement can further be achieved by the antenna structure comprising at least one sharp corner. Preferably, the antenna is arranged in an array (periodical or aperiodical) in order to increase the intensity of the antenna response by combining the response of several antennas.

The object is also solved by an (opto-) electronic system operating in the THz frequency range comprising such a THz frequency range antenna. The electronic system achieves the advantages which have been described above with respect to the THz frequency range antenna. Preferably, the system is one of a sensing system, a communication system, an imaging system, a signal processing system, and a light modulating system.

The object is also solved by a system for distinguishing between a THz signal and background noise comprising: a modulator comprising a THz frequency range antenna according to any one of claims 1 to 11, the modulator being adapted such that the resonance of surface plasmons in the region of the THz frequency range antenna is tuned with a predetermined modulation rate, and the system further comprising: a detector being controlled by the predetermined modulation rate. In this case, the detector is locked onto the modulation provided to the THz frequency range antenna. Thus, detection with high selectivity and high sensitivity is achieved.

The object is also solved by a method for tuning the response of a THz frequency range antenna according to claim 15. The method comprises the step tuning the response by changing the geometry of the antenna structure or by changing material characteristics of the semiconductor film. The geometry of the antenna structure can for example be changed during operation by exploiting a piezoelectric structure. The material characteristics of the semiconductor film which can be changed comprise for instance the carrier concentration, the carrier mobility and the like.

BRIEF DESCRIPTION OF THE DRAWINGS

Further features and advantages of the present invention will arise from the detailed description of embodiments with reference to the enclosed drawings.

FIG. 3a illustrates electric field intensities of surface plasmon resonances for an antenna structure similar to FIG. 2a.

FIG. 3b illustrates electric field intensities of surface plasmon resonances for an antenna structure similar to FIG. 2b.

DETAILED DESCRIPTION OF EMBODIMENTS

Figure 1:
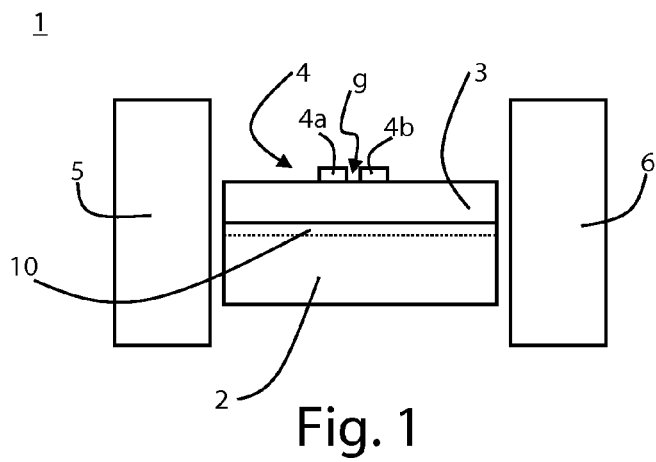
FIG. 1 schematically shows a THz frequency range antenna together with a THz frequency generator and a THz frequency detector in a side view.

An embodiment will now be described with reference to the figures. The THz frequency range antenna 1 according to the embodiment is schematically shown in FIG. 1. The THz frequency range antenna 1 comprises a substrate 2 on which a thin semiconductor film 3 is deposited. The substrate 2 is made from a material which is transparent with respect to electromagnetic radiation having frequencies in the THz frequency range, such as quartz or other such material. The semiconductor film 3 has a thickness d (in the vertical direction in FIG. 1, i.e. in the direction vertical to the plane in which the substrate extends) of several μm, e.g. between 0.5 μm and 100 μm, possibly up to 300 μm. According to the embodiment, the semiconductor film 3 comprises InSb (Indium/Antimony) as a base material. However, the semiconductor film 3 is not restricted to pure InSb but doped material is also possible and can even be preferred as will become apparent from the following description. The semiconductor film 3 can be deposited on the substrate 2 in a plurality of manners known in the art, such as sputtering, evaporation, vapor deposition, and the like. Further, the semiconductor film 3 can be annealed as known in the art for fine tuning of the semiconductor material properties.

As an alternative to the described InSb, the semiconductor film 3 can also be formed by InAs (Indium Arsenide) as a base material or by another suitable semiconductor material. However, it should be noted that InSb and InAs are preferred base materials due to their low bandgap, low electron effective mass, and high electron mobility. As will become apparent from the following description, these features allow sharp and well defined surface plasmon resonances. The semiconductor film 3 is chosen because the permittivity at THz frequencies of the material is suitable to invoke a collective motion of electrons at interfaces (surface plasmon polaritons). Thus, in this respect the materials show properties at THz frequencies similar to those of metals at optical frequencies.

The surface of the semiconductor film 3 is processed with an antenna structure 4. The antenna structure 4 is provided to the semiconductor film 3 by known semiconductor processing techniques such as optical lithography and dry and/or wet etching. The antenna structure 4 consists of the same material as the semiconductor film 3 and is structured in or on the surface thereof, respectively. Preferably the semiconductor film is completely etched/cut through and the antennas are separated from each other by dielectric, the antennas protruding from the surface. The antenna structure 4 can be fabricated by known microfabrication techniques available in thin film facilities.

Figure 2:
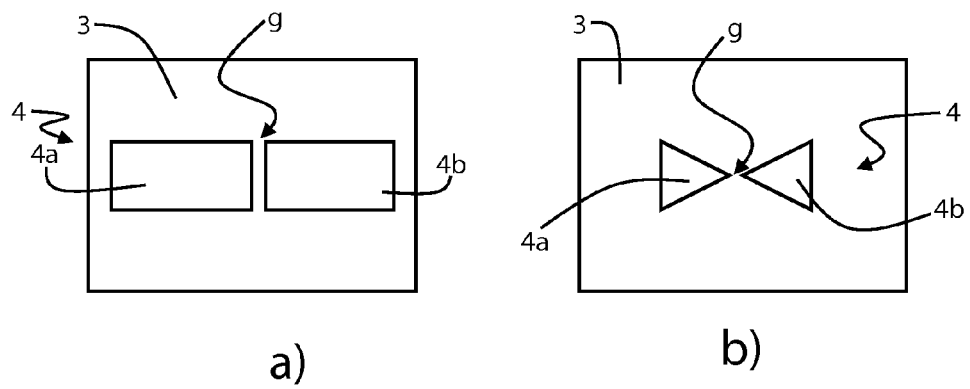
FIG. 2a schematically shows the region of an antenna structure of the THz frequency range antenna in a first realization in top view.
FIG. 2b schematically shows the region of an antenna structure of the THz frequency range antenna in a second realization in top view.

According to the embodiment, the antenna structure 4 comprises two elements 4a and 4b which are located spaced from each other by a small gap g in a direction along the surface of the semiconductor film 3. The elements 4a and 4b may comprise many different shapes when viewed from on top of the surface of the semiconductor film 3, as will be described with reference to FIGS. 2a and 2b. Two examples for the shape of the antenna structure 4 are schematically shown in FIGS. 2a and 2b, respectively. It should be noted however that the shapes shown in FIGS. 2a and 2b are only examples and not intended to limit the scope of this disclosure. Many other shapes are possible. The two elements 4a and 4b are arranged such that the gap g is oriented along the direction of excitation of surface plasmons in the semiconductor film 3.

FIG. 2a shows an example in which the elements 4a and 4b of the antenna structure 4 each have the shape of a rectangle, while FIG. 2b shows an example in which the elements 4a and 4b of the antenna structure 4 each have the shape of a triangle (with the edges of the respective triangles pointing towards each other and enclosing the gap g). Since the antenna structure 4 comprises the elements 4a and 4b spaced by the gap g, it forms a dipole antenna. It should be noted that sharp corners of the elements 4a and 4b (such as in the case of FIG. 2b) are preferred due to the fact that sharp corners result in an advantageously enhanced electric field in the gap region as will be described below.

The elements 4a and 4b of the antenna structure 4 comprise dimensions between 10 μm to 1000 μm in the directions in parallel to the surface of the semiconductor film 3. In the direction vertical to the surface of the semiconductor film 3, the antenna structure 4 comprises dimensions between 0.5 μm and 100 μm, possibly up to 300 μm. The gap g has a width Δ (from element 4a to element 4b) between 10 nm and 10 μm.

For example, the THz frequency range antenna 1 can be arranged between a THz frequency generator 5 and a THz frequency detector 6, as schematically depicted in FIG. 1. It should be noted that the THz frequency generator 5 and the THz frequency detector 6 are only schematically shown in FIG. 1. The THz frequency generator 5 generates surface plasmons in the THz frequency range on the structured semiconductor film 3. The THz frequency range detector 6 is adapted to detect THz frequency surface plasmons. The THz path formed by the THz frequency range generator 5 and the THz frequency range detector 6 can e.g. make use of a femtosecond laser and nonlinear crystals or be integrated in a compact, all-electronic version.

It has been found that antenna structures 4 as described above are capable of locally enhancing the electric field close to the antenna structure. Further, with such antenna structures 4 it is possible to concentrate the field in the gap between the elements 4a and 4b and achieve giant field enhancements in the order of $10^3$ times the intensity of an incident field. These effects are due to generation of plasmonic resonances in the THz frequency range. The concentration of the field and the field enhancement induce an enhancement of the interaction of the electromagnetic THz radiation with material placed in the region of the antenna. This effect can be exploited for achieving improved sensitivity in chemical compound sensing applications (for the example of the THz frequency range antenna being used in sensing applications). The achieved plasmonics resonance of the antennas is characterized by a spectral resonance in the scattering cross-section. Thus, according to the embodiments THz frequency range antennas made from semiconductor material are provided which support plasmonic resonances in the THz frequency range. With regard to sensing applications, operation in the THz frequency range is very advantageous because of the inherent selectivity of the sensors due to the particular spectral signatures of molecules in the THz frequency range.

The described THz frequency range antennas present characteristic resonant features in the far field spectrum. The extinction cross-section of the THz frequency range antennas presents an enhancement around the resonance frequency of the surface plasmons. This can be detected in a transmission experiment, for example. Changes in the shape of the extinction cross-section appear by interaction with the surrounding environment. For instance, in particular the presence of a gas having strong absorption lines in the region of interest can be detected with the described THz frequency range antennas.

The described giant enhancement of the electromagnetic field located around the gap has applications where a strong THz frequency field is required. For example, nonlinear effects will be enhanced as a result of the stronger interaction between the electromagnetic field and matter present in that region. Thus, with regard to sensor applications an increased sensitivity of the sensors will result.

Figure 3:
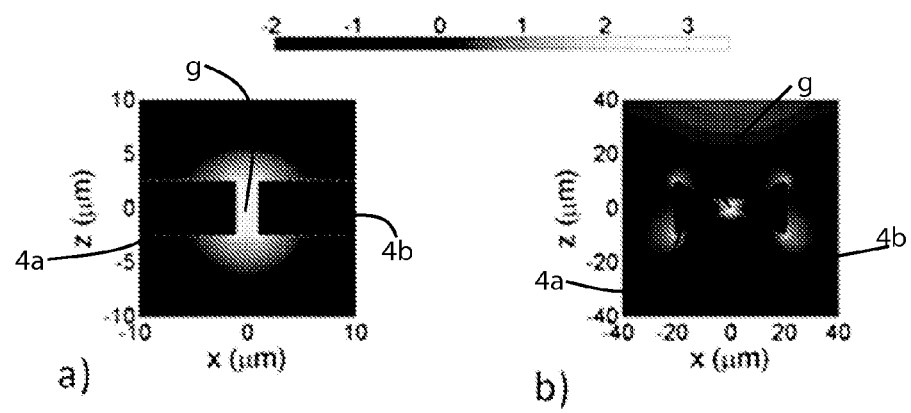

Examples for the achieved electric field enhancement in the region of the gap g of such THz frequency range antennas will be given with reference to FIGS. 2a and 2b. FIG. 3a depicts the near-field intensity distribution of the electric field at a frequency of 1.62 THz on a logarithmic scale for an InSb antenna having a rectangular shape. The horizontal axis corresponds to a first axis in parallel to the surface of the semiconductor film 3 and the vertical axis corresponds to the height of the antenna, perpendicular to the interface with the dielectric. The displayed results are obtained from 2D calculations using an electromagnetic field solver. It has been demonstrated that 2D calculations of the antenna cross sections properly describe 3D structures (O. L. Muskens, J. Gomez-Rivas, V. Giannini, and J. A. Sanchez-Gil, "Optical scattering resonances of single and coupled dimer plasmonic nanoantennas" Opt. Expr. Vol. 15, pp. 17736-17746, December 2007). The grey-scale corresponds to the electric field intensity normalized to the incident field intensity. The elements 4a and 4b and the gap g can be clearly seen in the illustration. As can be seen in FIG. 3a, giant enhancement of the electric field in the region of the gap g occurs.

FIG. 3b shows a corresponding illustration for a triangular (bow-tie) shape of the elements 4a and 4b at a frequency of 2 THz. It can be seen that giant electric field enhancement occurs in the region of the gap g.

Thus, with the THz frequency range antennas described, the excitation of the plasmonic resonance induces, in the near-field, a strong electric field with an enhancement factor of several orders of magnitude in the gap of the antenna structure 4. This enhancement is the sign of an increased interaction of the antenna structure 4 with an incoming electric field.

A further feature of the presented THz frequency range antenna will be described in the following. Due to the THz frequency range antenna 1 being formed from semiconductor material, the features of the THz frequency range antenna can be easily modified in a plurality of manners.

It has been found that the plasmonic resonances strongly depend on the shape, the size, and the dielectric constant of the material used to make the antenna as well as on its dielectric environment. In particular, field enhancements and magnitude of the extinction cross-sections are very much dependent on the geometry of the antenna. The resonance condition depends on several geometrical parameters such as the length and width of the antenna structure, the thickness of the antenna structure, and the gap width. With known semiconductor processing techniques the shape of the elements 4a and 4b of the antenna structure 4, the size of the elements 4a and 4b and the width of the gap g can conveniently be defined at the processing stage.

Figure 4:
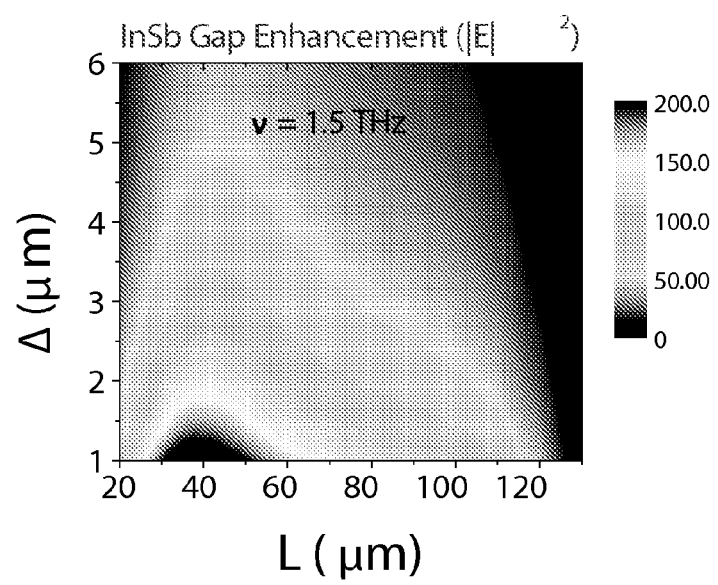
FIG. 4 illustrates the achieved enhancement of the electric field intensities in the gap region for an antenna structure similar to FIG. 2a for different dimensions of the antenna structure.

Referring to FIG. 4, it will be shown how the achieved enhancement of the electric field in the region of the gap g depends on the dimensions of the antenna structure 4. FIG. 4 depicts the achieved gap field enhancement $|E|^2$ in greyscale for a rectangular antenna structure 4 (similar to FIG. 2a) as a function of the length L (on the x-axis) and of the gap width $\Delta$ (on the y-axis) for a frequency of 1.5 THz. As can be seen from FIG. 4, a variation of the parameters L and $\Delta$ induces a strong variation of the field enhancement in the gap g of the antenna structure 4. In particular, large enhancements of the electric field in the gap g are achieved for 30 µm<L<50 µm and $\Delta$<1.5 µm. It should be noted that the variation of the gap width D from 3 µm to less than 1 µm results in a change in the enhancement of the electric field in the gap g of one order of magnitude. It has been found that, as a general rule, an enlarged enhancement of the electric field in the gap g is achieved when the width $\Delta$ of the gap g is reduced. Further, large enhancements of the electric field in the region of the gap can be achieved with gap widths in the order of 100 nm or less.

To summarize, it has been found that reducing the width of the gap g increases the field strength resulting in higher sensitivity. Similarly, one or more sharp corners in the antenna structure 4 also enhance the field strength and thus sensitivity (cf. FIG. 3b).

Exploiting semiconductor processing techniques, a THz frequency range antenna can be provided the gap width of which can be varied during operation. In this case, the THz frequency range antenna comprises a gap g with an adjustable width $\Delta$. For example, this can be achieved using piezoelectric materials which allow varying the width of the gap by application of a (static) electric field. For example, the piezoelectric material can be used as the substrate or an intermediate layer of piezoelectric material 10 can be provided, e.g. between the substrate 2 and the semiconductor film 3. The latter case is schematically indicated by a dotted line in FIG. 1. In these cases, the gap g of the antenna structure 4 can be electrically controlled.

Further, when the width $\Delta$ of the gap g decreases, the central wavelength of the surface plasmon resonance becomes shifted. Thus, the position of this central wavelength can be tuned by changing the gap width $\Delta$.

Figure 5:
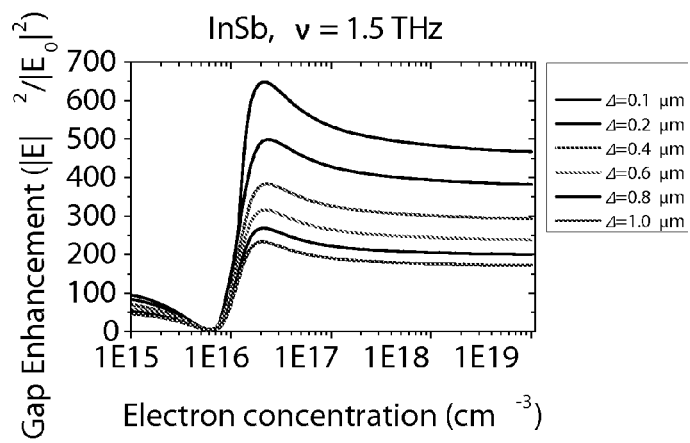
FIG. 5 illustrates the enhancement of the electric field in the gap in dependence on the electron concentration for different gap widths.

As an alternative or additionally, the properties of the THz frequency range antenna 1 can be modified by changing the carrier concentration or the carrier mobility in the semiconductor film 3 and/or in the antenna structure 4. FIG. 5 illustrates the dependency of the enhancement of the electric field in the gap (on the y-axis) as a function of the electron concentration (on the x-axis) for different widths $\Delta$ of the gap g. FIG. 5 shows this dependency for InSb as semiconductor material and for a frequency of 1.5 THz. It can be seen that the behavior of the plasmonic THz frequency range antenna 1 is strongly dependent on the electronic properties of the semiconductor material. Thus, the actually occurring enhancement of the electric field in the gap g can be controlled by changing the carrier concentration. Further, the position of the resonance frequency of the THz frequency range antenna 1 can be changed by changing the carrier concentration. This means, the THz frequency range antenna 1 can be tuned by changing the carrier concentration. This results in the possibility to adjust the spectral position of the resonance and therefore the overlap with spectroscopic features to be detected. As a consequence this leads to increased sensitivity.

Changing the carrier concentration can e.g. be realized by changes in temperature (allowing slow modulation/slow changes), by optical excitation (allowing fast modulation/fast changes), electrically via carrier injection (allowing fast modulation/fast changes), and the like.

Figure 6:
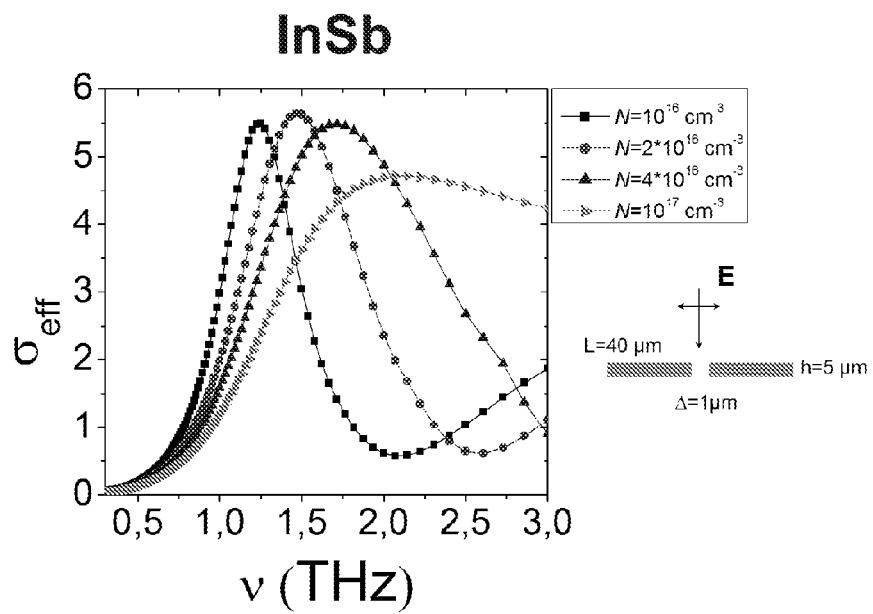
FIG. 6 illustrates the normalized scattering cross-section in dependence on frequency for different charge carrier densities.

Further, by changing the carrier concentration, the scattering cross-section of the THz frequency range antenna 1 can be changed, as can be seen in FIG. 6. FIG. 6 illustrates the normalized scattering cross-section for an InSb-based THz frequency range antenna comprising an antenna structure 4 with rectangular elements 4a and 4b. FIG. 6 shows the dependence of the scattering cross-section (on the y-axis) as a function of the frequency (on the (x-axis) for different carrier concentrations (different symbols). The values correspond to an antenna structure with a gap width $\Delta$ of 1 µm, lengths of the elements 4a and 4b of 40 µm and a height of the antenna structure of 5 µm.

In a similar manner as has been described with respect to tuning of the THz frequency range antenna 1 by changing the carrier concentration, the properties of the THz frequency range antenna 1 can be adjusted by changing the carrier mobility in the semiconductor material.

As a consequence, a THz frequency range antenna 1 is provided which offers the possibility to actively modify/tune the resonance and therefore to tune both the enhancement and the scattering cross-section. Such a THz frequency range antenna 1 is suitable for many applications.

For instance, the possibility of actively modifying the resonance can be used to tune the enhancement of the electrical field at a particular frequency. This feature can be used to distinguish between a signal at a specific THz frequency and a background noise for sensitivity enhancement by tuning the resonance in the region of the antenna structure 4 with a known modulation rate and locking a detector onto this tuned signal.

On the other hand, the possibility of actively modifying the resonance can be used to modify the frequency at which the field enhancement occurs to scan through spectroscopic features. These features can be conveniently exploited in active sensors and modulators.

According to one aspect, a tunable THz transmitter can be realized, as will now be described. First, the THz frequency range antenna 1 is designed for a certain operating range (by exploiting the possibilities of the manufacturing process as outlined above). A typical linewidth of the resonance in the far field would be about 1 THz. The central wavelength of the antenna can be designed by changing length, width, or thickness of the antenna structure 4. Then, post fabrication, an "in-operation" tuning can be achieved by varying the gap width Δ, as has been explained above. This can for instance be achieved using piezoelectric materials. When the width Δ of the gap g decreases the central wavelength of the surface plasmon resonance is shifted. In other words, when moved away from resonance, the magnitude of the field enhancement decreases. In this way, a dynamic operation of the THz frequency range antenna 1 is enabled. Further, the THz frequency range antenna 1 can be tuned by changing the carrier concentration and/or carrier mobility, as has been described above.

Thus, a novel electromagnetic THz frequency range antenna based on semiconductor materials is provided which enables an active control of both the field enhancement (sensitivity) and the position of the resonance for spectrum scanning and modulation.

When the THz frequency range antenna 1 is used for sensing applications, an object to be sensed can be concentrated to the antenna gap g where the electric field is giantly enhanced. Thus, the region of the gap g can be functionalized as a sensing element.

Besides application to sensing systems such as THz spectroscopy devices which will benefit from the increased sensitivity, the THz frequency range antenna 1 can also be used in many other applications such as communication systems, imaging systems, signal processing systems, light modulation systems, and the like. The THz frequency range antenna 1 can e.g. be used in sensors for chemical (gas) detection and/or biological detection, in inspection tools for inspection of organic materials such as polymers and small molecules, for non-destructive inspection of organic or electronic materials, in imaging systems, in medical systems (such as for inspection of biological materials), in modulators for communication devices, in biomedical diagnostic devices (e.g. for breath analysis), and the like.

Localization of the THz radiation to sub-wavelength volumes which is achieved by the proposed small gap of the antenna structure 4 opens the path to the local inspection of material responding to electromagnetic radiation in the THz frequency range. As a result, an enhanced sensitivity and sub-wavelength inspection down to the order of 1 μm becomes available.

The invention claimed is:

1. A THz frequency range antenna comprising:
a semiconductor film having a surface adapted to exhibit surface plasmons in the THz frequency range,
wherein the surface of the semiconductor film is structured to form an antenna structure arranged to support localized surface plasmon resonances in the THz frequency range, the antenna structure having a gap (g) which is controlled for varying at least one dimension thereof.

2. The THz frequency range antenna according to claim 1, wherein the antenna structure comprises at least two elements structured in or on the surface of the semiconductor film and spaced from each other in a direction in parallel to the surface of the semiconductor film by the gap (g).

3. The THz frequency range antenna according to claim 2, wherein the at least one dimension of the gap (g) is the width (Δ), wherein the width (Δ) is in the range between 10 nm and 10 μm, preferably between 50 nm and 200 nm.

4. The THz frequency range antenna according to claim 1, wherein the antenna structure consists of the same material as the semiconductor film.

5. The THz frequency range antenna according to claim 1, characterized in that a functionalized surface adapted to attach pre-determined molecules is provided in a region around the antenna structure and/or in a region around the gap (g).

6. The THz frequency range antenna according to claim 1, wherein the semiconductor film has a thickness in the range between 0.5 μm and 300 μm, preferably between 0.5 μm and 100 μm.

7. The THz frequency range antenna according to claim 1, wherein the semiconductor film is arranged on a substrate which is transparent for electromagnetic radiation in the THz frequency range.

8. The THz frequency range antenna according to claim 1, which is adapted for being inserted between a THz frequency generator and a THz frequency detector.

9. The THz frequency range antenna according to claim 1, wherein the piezoelectric material is used as a piezoelectric substrate or is provided as an piezoelectric intermediate layer between the semiconductor film and the substrate.

10. The THz frequency range antenna according to claim 1, wherein the semiconductor film comprises InSb or InAs as a base material.

11. The THz frequency range antenna according to claim 1, wherein the antenna structure is arranged such that an electric field of the surface plasmon resonances is locally enhanced in the region of the antenna structure.

12. An electronic system operating in the THz frequency range comprising a THz frequency range antenna, said antenna comprising:
a semiconductor film having a surface adapted to exhibit surface plasmons in the THz frequency range,
wherein the surface of the semiconductor film is structured to form an antenna structure arranged to support localized surface plasmon resonances in the THz frequency range, the antenna structure having a gap (g) which is controlled for varying at least one dimension thereof.

13. The electronic system according to claim 12, wherein the system is one of a sensing system, a communication system, an imaging system, a signal processing system, and a light modulating system.

14. A system for distinguishing between a THz signal and background noise, comprising
a modulator comprising a THz frequency range antenna, the modulator being adapted to tune the resonance of surface plasmons in the region of the THz frequency range antenna on and off by varying the gap width with a predetermined modulation rate, and
a detector being controlled by the predetermined modulation rate, wherein the THz frequency range antenna comprises:
a semiconductor film having a surface adapted to exhibit surface plasmons in the THz frequency range, wherein the surface of the semiconductor film is structured to form an antenna structure arranged to support localized surface plasmon resonances in the THz frequency range, wherein the semiconductor film is provided on a piezoelectric material.

15. A method for tuning the response of a THz frequency range antenna, wherein the method comprises the step:
tuning the response by varying at least one dimension of a gap of the THz frequency range antenna, wherein the THz frequency range antenna comprises:
a semiconductor film having a surface adapted to exhibit surface plasmons in the THz frequency range,
wherein the surface of the semiconductor film is structured to form an antenna structure arranged to support localized surface plasmon resonances in the THz frequency range.

\* \* \* \* \*